United States Patent [19]

Dugan

[11] Patent Number: Plant 6,127

[45] Date of Patent: Mar. 15, 1988

[54] EUONYMUS PLANT NAMED MOONSHADOW

[75] Inventor: Thomas F. Dugan, Perry, Ohio

[73] Assignee: Dugan Nurseries, Incorporated, Perry, Ohio

[21] Appl. No.: 833,052

[22] Filed: Feb. 25, 1986

[51] Int. Cl.[4] ..... A01H 5/00

[52] U.S. Cl. ..... Plt./63

[58] Field of Search ..... Plt. 63

*Primary Examiner*—Robert E. Bagwill

*Attorney, Agent, or Firm*—Schwartz, Jeffery, Schwaab, Mack, Blumenthal & Evans

[57] ABSTRACT

The new cultivar Moonshadow is especially characterized by its broadleaf evergreen foliage which has pronounced yellow centers that cover the entire leaf except for narrow dark green margins, with the leaves inside the plant being of the same variegated color as the stem tips, thereby giving the plant as a whole a distinctive and striking light yellow appearance, accented delicately by the narrow green curled leaf margins.

2 Drawing Figures

The present invention comprises a new and distinctive cultivar of Euonymus plant, botanically known as *Euconymus fortunei*, and hereinafter referred to by the cultivar name Moonshadow.

Moonshadow is a sport of the Euonymus plant known by the cultivar name Sunspot, disclosed in U.S. Plant Pat. No. 4,340. Moonshadow was discovered by me in Perry, Ohio, in a cultivated area in which plants of the parent cultivar Sunspot were being grown. Moonshadow was discovered in the form of two nodes on the segment of a branch of the parent cultivar in which the foliage showed improved variegation. The sport was also observed due to the unique showing of a larger golden spot in the center of the green leaf, and by the stems of the plant being yellow in color. Continued observation of the sport, as well as the subsequent asexually reproduced plants thereof, convinced me that the sport is both new and distinct from the parent cultivar, as well as from all other cultivars of Euonymus plants of which I am aware.

The following unique combination of characteristics have been repeatedly observed and serve to distinguish Moonshadow as a new and distinct cultivar:

1. A distinctive variegation pattern in which a yellow spot or area covers all of the leaf except for a narrow green margin around the outer edge of the leaf.
2. Green curled or wavy leaf margins.
3. Very short stem internodes, giving the overall plant a densely foliated appearance with very little bare stem showing.
4. Unusually light yellow stem color.
5. Semi-dwarf vigor, slower growing than the parent cultivar.
6. An attractive overall foliage texture due to the combination of wavy leaves and dense foliation.
7. A low broad habit, in contrast to the upright rounded habit of the parent cultivar.

Asexual reproduction of Moonshadow by me commencing in October, 1981 in Perry, Ohio by cuttings has established that the foregoing characteristics and distinctions come true to form and are established and transmitted through succeeding generations.

The accompanying photographic drawings illustrate, on sheet 1, a typical two year old specimen plant of the new cultivar in perspective view.

Sheet 2 comprises a close-up photograph of a group of branches of Moonshadow showing in more detail the leaf and stem characteristics. The color in the photographs is as nearly true as possible in color renditions of this type. The photographs were taken outdoors in Lansing, Mich. between 1:00 and 3:00 p.m. in mid-winter.

The following is a detailed description of the new cultivar, with color values being referenced to The Royal Horticultural Society Colour Chart, except where general color terms of ordinary dictionary significance are used. The color values were taken in Ashtabula, Ohio at approximately 10:00 a.m. on Jan. 8, 1986.

Form: Low, rounded, very dense, compact, slow growing; lower, broader and more compact than the parent cultivar Sunspot.

Growth:

*Two year plants.*—Height, from about 10 to 12 inches; breadth, from about 12 to 15 inches.

*Mature plants.*—Height, from about 2 to 3 feet; breadth, from about 2.5 to 3.5 feet.

Hardiness: Good winter hardiness is evidenced by the fact that plants grown outdoors have withstood winter temperatures of U.S.D.A. hardiness zone 5 with little protection, and U.S.D.A. hardiness zone 4 with some wind protection.

Stems (branchlets): Smooth, dull; color, intense yellow, Group 10B, with little or no green streaking. Short internodes from 2 to 10 mm. Finely textured; from 2 to 5 mm. in diameter. Occasional aerial roots.

Axillary buds: Tiny, elongate, conical, less than 2 mm. long.

Foliage:

*Type.*—Broadleaf evergreen, petioled, opposite.

*Shape.*—Ovate to elliptic.

*Petioles.*—Length, 1 to 2 mm.; color yellow group 10B.

*Size of leaf.*—Length from 1.5 to 4.0 cm.; breadth from 1.0 to 1.5 cm.

*Leaf texture.*—Slightly thinner and much more wavy or curled than the parent plant Sunspot; smooth, upper surface glossy; lower surface dull.

*Veining.*—On leaf underside only the midrib is visibly veined; on leaf upper surface, veins are difficult to see.

*Leaf margins.*—Crenate, serrate.

*Color.*—Center of leaf, upper side vivid Yellow Group 10 between B and C, covers all but a thin area around leaf edge, with areas of stronger concentration toward Yellow 10-B. Center of leaf, under side, Yellow Group 1-D. Edges of leaf, upper side Deep Green Group 139-A-B. Edges of leaf, under side, Deep Green Group 139 between B and C. On newly expanding leaves all colors tend towards a lighter green, but darken quickly so that new leaves when fully expanded are very close in color to the oldest leaves on a given plant.

Flower: No flowers have been observed on plants of Moonshadow grown to date.

I claim:

1. A new and distinct cultivar of Euonymus plant known by the cultivar name Moonshadow, as illustrated and described, and characterized particularly as to uniqueness by the combined characteristics of low, rounded, compact and shapely habit of growth; good winter hardiness, and thick broadleaf evergreen foliage having pronounced large yellow centers with very thin dark green margins of irregular depth, with the leaves inside the plant being of the same variegated color as the stem tips, thereby giving the plant as a whole a distinctive and striking light yellow spotted appearance, with curly leaf texture.

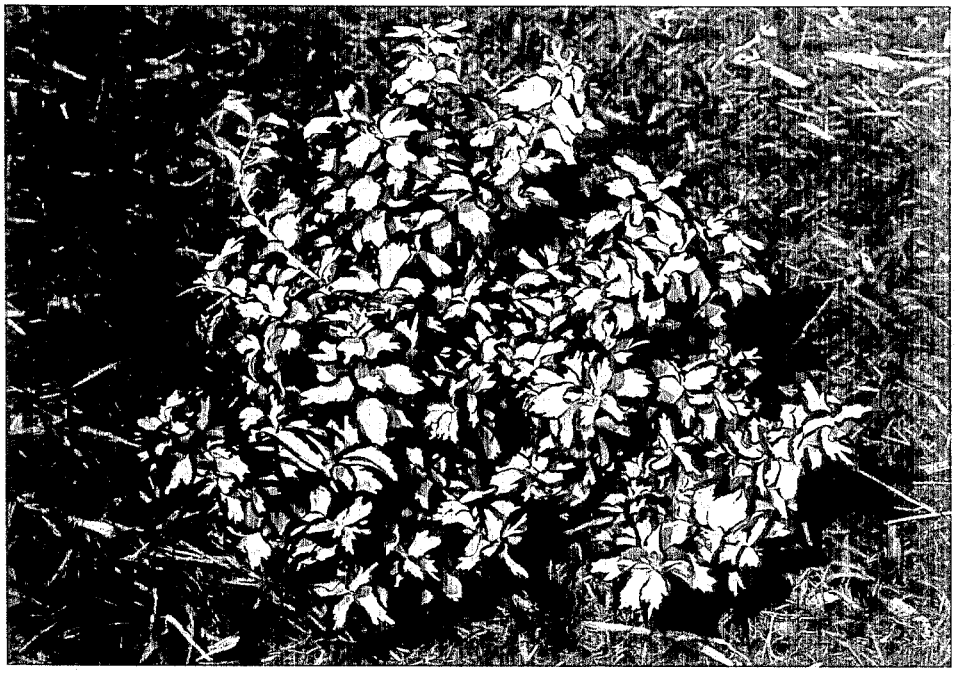

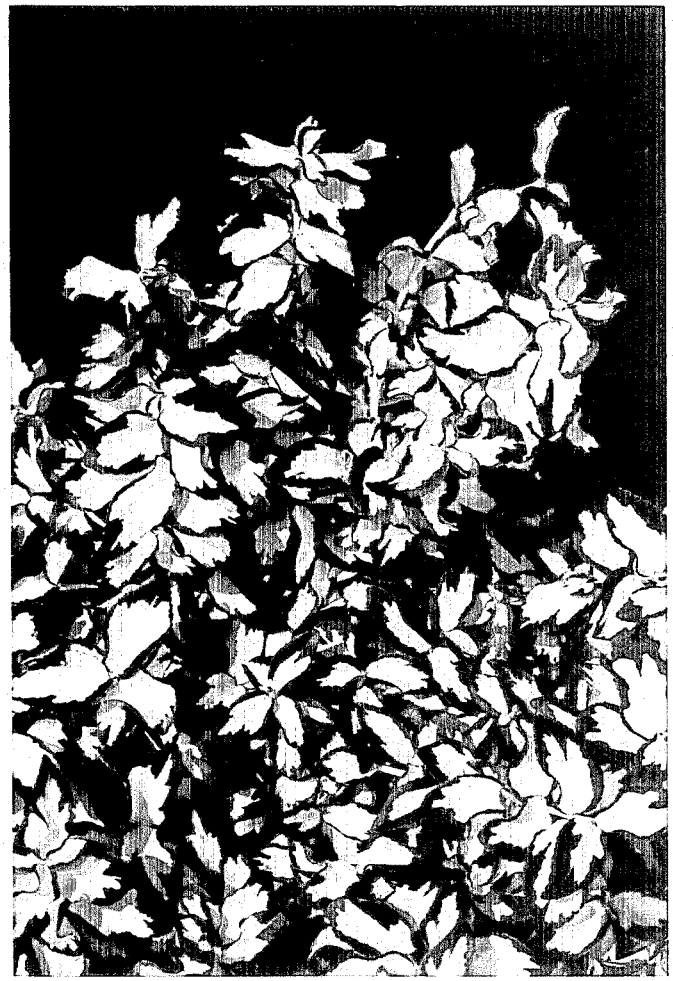

* * * * *